US005576317A

United States Patent [19]

Gonsalves

[11] Patent Number: 5,576,317
[45] Date of Patent: Nov. 19, 1996

[54] NK-1 RECEPTOR ANTAGONISTS AND 5HT$_3$ RECEPTOR ANTAGONISTS FOR THE TREATMENT OF EMESIS

[75] Inventor: Susan F. Gonsalves, Stonington, Conn.

[73] Assignee: Pfizer Inc., New York, N.Y.

[21] Appl. No.: 353,049

[22] Filed: Dec. 9, 1994

[51] Int. Cl.$^6$ .................. A61K 31/535; A61K 31/44; A01N 43/90

[52] U.S. Cl. .................. 514/231.2; 514/305; 514/306; 514/314; 514/315; 514/326; 514/327; 514/329; 514/331; 514/336; 514/344; 514/345; 514/349; 514/350; 514/438; 514/443; 514/444; 514/461; 514/468; 514/816; 514/872

[58] Field of Search .................. 514/231.2, 305, 514/306, 314, 315, 326, 327, 329, 331, 336, 344, 345, 349, 350, 438, 449, 444, 461, 468, 816, 872

[56] References Cited

FOREIGN PATENT DOCUMENTS

615751A1  8/1994  European Pat. Off. .

Primary Examiner—Nathan M. Nutter
Attorney, Agent, or Firm—Peter C. Richardson; Paul H. Ginsburg; Karen DeBenedictis

[57] ABSTRACT

The present invention relates to a method of treating or preventing emesis in a mammal, including a human, by administering to the mammal a 5HT$_3$ receptor antagonist and an NK-1 receptor antagonist (e.g., a substance P receptor antagonist). It also relates to pharmaceutical compositions containing a pharmaceutically acceptable carrier, a 5HT$_3$ receptor antagonist and an NK-1 receptor antagonist.

14 Claims, 1 Drawing Sheet

Figure 1

NK-1 RECEPTOR ANTAGONISTS AND 5HT₃ RECEPTOR ANTAGONISTS FOR THE TREATMENT OF EMESIS

The present invention relates to a method of treating or preventing emesis in a mammal, including a human, by administering to the mammal a $5HT_3$ receptor antagonist and an NK-1 receptor antagonist (e.g., a substance P receptor antagonist). It also relates to pharmaceutical compositions containing a pharmaceutically acceptable carrier, a $5HT_3$ receptor antagonist and an NK-1 receptor antagonist.

Identification of the antiemetic properties of $5HT_3$ receptor antagonists such as granisetron, ondansetron and tropisetron has greatly improved the clinical management of nausea and vomiting associated with cancer chemotherapy. The $5HT_3$ receptor antagonists do not, however, block nausea and vomiting in all patients nor are they highly efficacious against delayed or anticipatory vomiting. More recent studies in animals have shown that selective NK-1 receptor antagonists such as (2S,3S)-3-methoxybenzylamino-2-phenylpiperidine (hereinafter also referred to as Compound 1), block emesis induced by a variety of centrally and peripherally acting emetogens, although at relatively high dosages. (See Bountra et al., *Eur. J. Pharmacol.*, "Antiemetic profile of a non-peptide neurokinin NK-1 receptor antagonist, CP-99,994, in ferrets", 249:R3-R4 (1993) and Tattersall et al., *Eur. J. Pharmacol.*, "The tachykinin NK-1 receptor antagonist CP-99,994 attenuates cis-platinum induced emesis in the ferret", 250:R5-R6 (1993)). The present inventor has found that the combined administration of an NK-1 receptor antagonist and a $5HT_3$ receptor antagonist overcomes the limitations of each given separately. The combination is therefore expected to be effective in cases where either agent alone would not be, e.g., in ondansetron-resistant emesis.

SUMMARY OF THE INVENTION

The present invention relates to pharmaceutical compositions for the treatment or prevention of emesis comprising a $5HT_3$ receptor antagonist, an NK-1 receptor antagonist and a pharmaceutically acceptable carrier.

This invention also relates to a method of treating or preventing emesis in a mammal, comprising administering to said mammal an antiemetic effective amount of a pharmaceutical composition comprising a $5HT_3$ receptor antagonist, an NK-1 receptor antagonist and a pharmaceutically acceptable carrier.

This invention also relates to a method of treating or preventing emesis in a mammal, comprising administering to said mammal a $5HT_3$ receptor antagonist and an NK-1 receptor antagonist in amounts that render the combination of such two active agents effective in the treatment or prevention of such disorder.

A preferred embodiment of this invention relates to a pharmaceutical composition for the treatment or prevention of emesis, as described above, wherein the $HT_3$ receptor antagonist is selected from ondansetron, tropisetron and granisetron.

Other preferred embodiments of this invention relate to pharmaceutical compositions for the treatment of emesis, such as those described above, wherein the NK-1 receptor antagonist is selected from the group consisting of:
(2S,3S)-3-(5-tert-butyl-2-methoxybenzyl)amino-2-(3trifluoromethoxyphenyl)piperidine;
(2S,3S)-3-(2-isopropoxy-5-trifluoromethoxybenzyl)amino-2-phenyl-piperidine;
(2S,3S)-3-(2-ethoxy-5-trifluoromethoxybenzyl)amino-2-phenyl-piperidine;
(2S,3S)-3-(2-methoxy-5-trifluoromethoxybenzyl)-amino-2-phenylpiperidine;
(2S,3S)-3(-5-tert-butyl-2-trifluoromethoxybenzyl)amino-2-phenylpiperidine;
2-(diphenylmethyl)-N-(2-methoxy-5-trifluoromethoxy-phenyl)methyl-1-azabicyclo[2.2.2]octan-3-amine;
(2S,3S)-3-[5-chloro-2-(2,2,2-trifluoroethoxy)-benzyl]amino-2-phenylpiperidine;
(2S,3S)-3-(5-tert-butyl-2-trifluoromethoxybenzyl)amino-2-phenylpiperidine;
(2S,3S)-3-(2-isopropoxy-5-trifluoromethoxybenzyl)amino-2-phenylpiperidine;
(2S,3S)-3-(2-difluoromethoxy-5-trifluoromethoxybenzyl)-amino-2-phenylpiperidine;
(2S,3S)-2-phenyl-3-[2-(2,2,2-trifluoroethoxybenzyl)-aminopiperidine;
(2S,3S)-2-phenyl-3-(2-trifluoromethoxybenzyl)]aminopiperidine;
cis-3-(2-chlorobenzylamino)-2-phenylpiperidine;
cis-3-(2-trifluoromethylbenzylamino)-2-phenyl-piperidine;
cis-3-(2-methoxybenzylamino)-2-(2-fluorophenyl)-piperidine;
cis-3-(2-methoxybenzylamino)-2-(2-chlorophenyl)-piperidine;
cis-3-(2-methoxybenzylamino)-2-(2-methylphenyl)-piperidine;
cis-3-(2-methoxybenzylamino)-2-(3-methoxyphenyl)-piperidine;
cis-3-(2-methoxybenzylamino)-2-(3-fluorophenyl)-piperidine;
cis-3-(2-methoxybenzylamino)-2-(3-chlorophenyl)-piperidine;
cis-3-(2-methoxybenzylamino)-2-phenylpiperidine;
cis-3-(2-methoxybenzylamino)-2-(3-methylphenyl)-piperidine;
cis-3-(2-methoxybenzylamino)-2-(4-fluorophenyl)-piperidine;
cis-3-(2-methoxybenzylamino)-2-(3-thienyl)-piperidine;
cis-3-(2-methoxybenzylamino)-2-phenylazacyclo-heptane;
3-(2-methoxybenzylamino)-4-methyl-2-phenylpiperidine;
3-(2-methoxybenzylamino)-5-methyl-2-phenylpiperidine;
3-(2-methoxybenzylamino)-6-methyl-2-phenylpiperidine;
(2S,3S)-3-(2-methoxybenzylamino)-2-phenylpiperidine;
(2S,3S)-1-(5-carboethoxypent-1-yl)-3-(2-methoxybenzylamino)-2-phenylpiperidine;
(2S,3S)-1-(6-hydroxy-hex-1-yl)-3-(2-methoxybenzylamino)-2-phenylpiperidine;
(2S,3S)-1-(4-hydroxy-4-phenylbut-1-yl)-3-(2-methoxybenzylamino)-2-phenylpiperidine;
(2 S,3S)-1-(4-oxo-4-phenylbut-1-yl)-3-(2-methoxybenzylamino)-2-phenylpiperidine;
(2S,3S)-1-(5,6dihydroxyhex-1-yl)-3-(2-methoxybenzylamino)-2-phenylpiperidine;
cis-3-(5-fluoro-2-methoxybenzylamino)-2-phenyl-piperidine;
(2S,3S)-1-[4-(4-fluorophenyl)-4-oxobut-1-yl]-3-(2-methoxybenzylamino)-2-phenylpiperidine;
(2S,3S)-1-[4-(4-fluorophenyl)-4-hydroxybut-1-yl]-3-(2-methoxybenzyl)-2-phenylpiperidine;
cis-3-(2-methoxy-5-methylbenzylamino)-2-phenyl-piperidine;
(2S,3S)-1-(4-benzamidobut-1-yl)-3-(2-methoxybenzylamino)-2-phenylpiperidine;
cis-3-(2-methoxynaphth-1-ylmethylamino)-2-phenyl-piperidine;
(2S,3S)-3-(2-methoxybenzylamino)-1-(5-N-methyl-carboxamidopent-1-yl)-2-phenylpiperidine;
(2S,3S)-1-(4-cyanobut-1-yl)-3-(2-methoxybenzylamino)-2-phenylpiperidine;
(2S,3S)-1-[4-(2-naphthamido)but-1-yl]-3-(2-methoxy-benzylamino)-2-phenylpiperidine;

(2S,3S)-1-(5-benzamidopent-1-yl)-3-(2-methoxybenzylamino)-2-phenylpiperidine;
(2S,3S)-1-(5-aminopent-1-yl)-3-(2-methoxybenzylamino)-2-phenylpiperidine;
(2S,3S)-3-(5-chloro-2-methoxybenzylamino)-2-phenyl-piperidine;
(2S,3S)-3-(2,5-dimethoxybenzylamino)-2-phenyl-piperidine;
cis-3-(3,5-difluoro-2-methoxybenzylamino)-2-phenyl-piperidine;
cis-3-(4,5-difluoro-2-methoxybenzylamino)-2-phenyl-piperidine;
cis-3-(2,5-dimethoxybenzylamino)-1-[4-(4-fluorophenyl)-4-oxobut-1-yl]-2-phenylpiperidine;
cis-3-(5-chloro-2-methoxybenzylamino)-1-(5,6-dihydroxyhex-1-yl)-2-phenylpiperidine;
cis-1-(5,6-dihydroxyhex-1-yl)-3-(2,5-dimethoxy-benzylamino)-2-phenylpiperidine;
cis-2-phenyl-3-[-2(prop-2-yloxy)benzylamino]piperidine;
cis-3-(2,5-dimethoxybenzyl)amino-2-(3-methoxy-phenyl)piperidine hydrochloride;
cis-3-(5-chloro-2-methoxybenzyl)amino-2-(3-methoxyphenyl)piperidine dihydrochloride;
cis-3-(5-chloro-2-methoxybenzyl)amino-2-(3-chloro-phenyl)piperidine dihydrochloride;
3-(2-methoxybenzylamino)-2,4-diphenylpiperidine;
cis-3-(2-methoxybenzylamino)-2-phenylpyrrolidine;
(2S,3S)-3-(5-ethyl-2-methoxybenzyl)amino-2-phenyl-piperidine;
(2S,3S)-3-(5-n-butyl-2-methoxybenzyl)amino-2-phenyl-piperidine;
(2S,3S)-3-(2-methoxy-5-n-propylbenzyl)amino-2-phenyl-piperidine;
(2S,3S)-3-(5-isopropyl-2-methoxybenzyl)amino-2-phenyl-piperidine;
(2S,3S)-3-(5-s-butyl-2-methoxybenzyl)amino-2-phenyl-piperidine;
(2S,3S)-3-(5-t-butyl-2-methoxybenzyl)amino-2-phenyl-piperidine;
(2S,3S)-3-(2-methoxy-5-phenylbenzyl)amino-2-phenyl-piperidine;
2,4-dimethylthiazole-5-sulfonic acid [4-methoxy-3-((2S, 3S)-2-phenylpiperidin-3-ylaminomethyl)phenyl]-methylamide;
N-(4,5-dimethylthiazol-2-yl)-N-[4-methoxy-3-((2S,3S)-2-phenylpiperidin-3-ylaminomethyl) phenyl]-methanesulfonamide;
{5-[(4,5-dimethylthiazol-2-yl)methylamino]-2-methoxybenzyl}-((2S,3S)-2-phenylpiperidin -3-yl)amine;
{5-(4,5-dimethylthiazol-2-yl)methylamino)-2-methoxybenzyl}-((2S,3S)-2-phenylpiperidin-3-ylamine;
4,5-dimethylthiazole-2-sulfonic acid methyl-[3-((2S,3S)-2-phenylpiperidin-3-ylaminomethyl) -4-trifluoromethoxyphenyl]-amide;
2,4-dimethylthiazole-5-sulfonic acid [4-isopropoxy-3-((2S, 3S)-2-phenylpiperidin-3-ylaminomethyl)phenyl]-methylamide;
2,4-dimethylthiazole-5-sulfonic acid [4-isopropoxy-3-((2S, 3S)-2-phenylpiperidin -3-ylaminomethyl)phenyl]-isopropylamide;
2,4-dimethylthiazole-5-sulfonic acid [4-methoxy-3-((2S, 3S)-2-phenylpiperidin-3-ylaminomethyl)phenyl]-isopropylamide;
2,4-dimethylthiazole-5-sulfonic acid [4-methoxy-3-((2S, 3S)-2-phenylpiperidin-3-ylaminomethyl)phenyl]-isobutylamide;
2,4-dimethylthiazole-5-sulfonic acid [4-isopropoxy-3-((2S, 3S)-2-phenylpiperidin -3-ylaminomethyl)phenyl]-isobutylamide;
(2S,3S)-N-(5-isopropyl-2-methoxyphenyl)methyl-2-diphenylmethyl-1-azabicyclo -[2.2.2]octan-3-amine;
(2S,3S)-N-(5-tert-butyl-2-methoxyphenyl)methyl-2-diphenylmethyl-1-azabicyclo [2.2.2]octan-3-amine;
(2S,3S)-N-(5-methyl-2-methoxyphenyl)methyl-2-diphenylmethyl-1-azabicyclo [2.2.2]octan-3-amine;
(2S,3S)-N-(5-ethyl-2-methoxyphenyl)methyl-2-diphenylmethyl-1-azabicyclo [2.2.2]octan-3-amine;
(2S,3S)-N-(5-isopropyl-2-methoxyphenyl)methyl-2-diphenylmethyl-1-azabicyclo [2.2.2]octan-3-amine;
(2S,3S)-N-(5-sec-butyl-2-methoxyphenyl)methyl-2-diphenylmethyl-1-azabicyclo [2.2.2]octan-3-amine;
(2S,3S)-N-(5-n-propyl-2-methoxyphenyl)methyl-2-diphenylmethyl-1-azabicyclo [2.2.2]octan-3-amine;
(3R,4S,5S,6S)-N,N-diethyl-5-(5-isopropyl-2-methoxy-benzylamino)-6-diphenylmethyl-1-azabicyclo[2.2.2]octane-3-carboxamid;
(3R,4S,5S,6S)-N, N-diethyl-5-(2,5-dimethoxybenzylamino)-6-diphenylmethyl-1-azabicyclo [2.2.2]octane-3-carboxamide;
(3R,4S,5S,6S)-5-(5-isopropyl-2-methoxybenzylamino)-6-diphenylmethyl-1-azabicyclo [2.2.2]octane-3-carboxylic acid;
(3R,4S,5S,6S)-5-(2-methoxy-2-methylthiobenzylamino)-6-diphenylmethyl-1-azabicyclo [2.2.2]octane-3-carboxylic acid;
(3R,4S,5S,6S)-5-(2,5-dimethoxybenzylamino)-6-diphenylmethyl-1-azabicyclo [2.2.2]octane-3-carboxylic acid;
(3R,4S,5S,6S)-5-(2-methoxy-5-methylbenzylamino)-6-diphenylmethyl-1-azabicyclo [2.2.2]octane-3-carboxylic acid;
(3R,4S,5S,6S)-5-(5-ethyl-2-methoxybenzylamino)-6-diphenylmethyl-1-azabicyclo [2.2.2]octane-3-carboxylic acid;
(3R,4S,5S,6S)-5-(2-methoxyl-5-n-propylbenzylamino)-6-diphenylmethyl-1-azabicyclo [2.2.2]octane-3-carboxylic acid;
(3R,4S,5S,6S)-5-(5-sec-butyl-2-methoxybenzylamino)-6-diphenylmethyl-1-azabicyclo [2.2.2]octane-3-carboxylic acid;
(3R,4S,5S,6S)-5-(5-N-methyl-methanesulfonylamino-2-methoxy-benzylamino)-6-diphenylmethyl-1-azabicyclo [2.2.2]octane-3-carboxylic acid;
(3R,4S,5S,6S)-5-(2-methoxy-5-methylsulfinylbenzyl-amino)-6-diphenylmethyl-1-azabicyclo[2.2.2]octane-3-carboxylic acid;
(3R,4S,5S,6S)-5-(2-methoxy-5-trifluoromethoxybenzyl-amino)-6-diphenylmethyl-1-azabicyclo[2.2.2]octane-3-carboxylic acid;
(3R,4S,5S,6S)-5-(2-methoxy-5-methylsulfonylbenzyl-amino)-6-diphenylmethyl-1-azabicyclo[2.2.2]octane-3-carboxylic acid;
(3R,4S,5S,6S)-5-(5-dimethylamino-2-methoxybenzylamino)-6-diphenylmethyl-1-azabicyclo[2.2.2]octane-3-carboxylic acid;
(3R,4S,5S,6S)-5-(5-isopropyl-2-methoxybenzylamino)-6-diphenylmethyl-1-azabicyclo[2.2.2]octane-2-carboxylic acid;
(3R,4S,5S,6S)-5-(2-methoxy-5-methylthiobenzylamino)-6-diphenylmethyl-1-azabicyclo[2.2.2]octane-2-carboxylic acid;
(3R,4S,5S,6S)-5-(2,5-dimethoxybenzylamino)-6-diphenylmethyl-1-azabicyclo[2.2.2]octane-2-carboxylic acid;
(3R,4S,5S,6S)-5-(2-methoxy-5-methylbenzylamino)-6-diphenylmethyl-1-azabicyclo[2.2.2]octane-2-carboxylic acid;
(3R,4S,5S,6S)-5-(5-ethyl-2-methoxybenzylamino)-6-diphenylmethyl-1-azabicyclo[2.2.2]octane-2-carboxylic acid;
(3R,4S,5S,6S)-5-(2-methoxyl-5-n-propylbenzylamino)-6-diphenylmethyl-1-azabicyclo[2.2.2]octane-2-carboxylic acid;
(3R,4S,5S,6S)-5-(5-sec-butyl-2-methoxybenzylamino)-6-diphenylmethyl-1-azabicyclo[2.2.2]octane-2-carboxylic acid;

(3R,4S,5S,6S)-5-(5-N-methyl-methanesulfonylamino-2-methoxybenzyl-amino)-6-diphenylmethyl-1-azabicyclo[2.2.2]octane-2-carboxylic acid;

(3R,4S,5S,6S)-5-(2-methoxy-5-methylsulfinylbenzyl-amino)-6-diphenylmethyl-1-azabicyclo[2.2.2]octane-2-carboxylic acid;

(3R,4S,5S,6S)-5-(2-methoxy-5-trifluoromethoxybenzyl-amino)-6-diphenylmethyl-1-azabicyclo[2.2.2]octane-2-carboxylic acid;

(3R,4S,5S,6S)-5-(2-methoxy-5-methylsulfonylbenzyl-amino)-6-diphenylmethyl-1-azabicyclo[2.2.2]octane-2-carboxylic acid; and (3R,4S,5S,6S)-5-(5-dimethylamino-2-methoxybenzy-lamino)-6-diphenylmethyl-1-azabicyclo[2.2.2]octane-2-carboxylic acid;

and the pharmaceutically acceptable salts of the foregoing compounds.

The foregoing compounds and their pharmaceutical acceptable salts are hereinafter also referred to as "the Group A NK-1 antagonists."

Other preferred embodiments of this invention relate to methods of treating or preventing emesis, such as those described above, wherein the 5HT$_3$ receptor antagonist is selected from ondansetron, tropisetron and granisetron.

Other preferred embodiments of this invention relate to methods of treating or preventing emesis, such as those described above, wherein the NK-1 receptor antagonist is selected from the Group A NK-1 antagonists.

DETAILED DESCRIPTION OF THE INVENTION

The treatment of emesis includes the treatment of nausea, retching and vomiting. Emesis includes acute emesis, delayed emesis and anticipatory emesis. Emesis may be induced by drugs such as cancer chemotherapeutic agents (e.g., cyclophosphamide, cisplatin, dacarbazine, procarbazine, hydroxyurea, carmustine, lomustine and chlorambucil), cytotoxic antibiotics (e.g., dactinomycin, doxorubicin, mitomycin-C and bleomycin), opioid analgesics (e.g., morphine), anti-metabolites e.g., cytarabine, methotrexate and 5-fluorouracil), vinca alkaloids (e.g., etoposide, vinblastine and vincristine), and other drugs such as ipecac. Emesis may also be induced by radiation sickness, radiation therapy, poisons, toxins such as those caused by metabolic disorders or by infection (e.g., gastritis), pregnancy, vestibular disorders such as motion sickness, post-operative sickness, gastrointestinal obstruction, reduced gastrointestinal motility, visceral pain (e.g., myocardial infarction or peritonitis), migraine, increased intracranial pressure or decreased intracranial pressure (e.g., altitude sickness).

The following references refer, collectively, to quinuclidine, piperidine, ethylene diamine, pyrrolidine and azanorbornane derivatives and related compounds that exhibit activity as substance P receptor antagonists which can be used, in combination with a 5HT$_3$ antagonist, in the pharmaceutical compositions and methods of this invention, and to methods of preparing the same: U.S. Pat. No. 5,162,339, which issued on Nov. 11, 1992; U.S. Pat. No. 5,232,929, which issued on Aug. 3, 1993; World Patent Application WO 92/20676, published Nov. 26, 1992; World Patent Application WO 93/00331, published Jan. 7, 1993; World Patent Application WO 92/21677, published Dec. 10, 1992; World Patent Application WO 93/00330, published Jan. 7, 1993; World Patent Application WO 93/06099, published Apr. 1, 1993; World Patent Application WO 93/10073, published May 27, 1993; World Patent Application WO 92/06079, published Apr. 16, 1992; World Patent Application WO 92/12151, published Jul. 23, 1992; World Patent Application WO 92/15585, published Sep. 17, 1992; World Patent Application WO 93/19064, published Sep. 30, 1993; World Patent Application WO 94/08997, published Apr. 28, 1994; World Patent Application WO 94/04496, published Mar. 3, 1994; United States Patent Application 988,653, filed Dec. 10, 1992; United States Patent Application 026,382, filed Mar. 4, 1993; U.S. patent application Ser. No. 123,306, filed Sep. 17, 1993, and U.S. patent application Ser. No. 072,629, filed Jun. 4, 1993. All of the foregoing World Patent Applications designate the United States and were filed in the U.S. Receiving Office of the PCT. The foregoing patents and patent applications are incorporated herein by reference in their entirety.

Other substance P receptor antagonists that can be used, together with a 5HT$_3$ antagonist, in the pharmaceutical compositions and methods of this invention are those compounds and pharmaceutically acceptable salts described in the following references: European Patent Application EP 499,313, published Aug. 19, 1992; European Patent Application EP 520,555, published Dec. 30, 1992; European Patent Application EP 522,808, published Jan. 13, 1993, European Patent Application EP 528,495, published Feb. 24, 1993, PCT Patent Application WO 93/14084, published Jul. 22, 1993, PCT Patent Application WO 93/01169, published Jan. 21, 1993, PCT Patent Application WO 93/01165, published Jan. 21, 1993, PCT Patent Application WO 93/01159, published Jan. 21, 1993, PCT Patent Application WO 92/20661, published Nov. 26, 1992, European Patent Application EP 517,589, published Dec. 12, 1992, European Patent Application EP 428,434, published May 22, 1991, and European Patent Application EP 360,390, published Mar. 28, 1990.

This invention relates both to methods of treating emesis in which the NK-1 receptor antagonist and the 5HT$_3$ receptor antagonist are administered together, as part of the same pharmaceutical composition, as well as methods in which these two active agents are administered separately as part of an appropriate dose regimen designed to obtain the benefits of the combination therapy. The appropriate dose regimen, the amount of each dose administered, and specific intervals between doses of each active agent will depend upon the subject being treated, the emetogen and the severity of the condition. Generally, in carrying out the methods of this invention, the NK-1 receptor antagonist will be administered to an average 70 kg adult human in an amount ranging from about 0.36 to about 8.6 mg per kg body weight of the subject being treated per day, in single or divided doses, preferably from about 0.36 to about 4.3 mg/kg, and the 5HT$_3$ receptor antagonist will be administered in an amount ranging from about 0.007 to about 0.17 mg per kg body weight of the subject being treated per day, in single or divided doses, preferably from about 0.007 to about 0.07 mg/kg/day when administered parenterally and from about 0.029 to about 0.17 mg/kg/day when administered orally. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The NK-1 receptor antagonists and the 5HT$_3$ receptor antagonists that are employed in the pharmaceutical compositions and methods of this invention are hereinafter also referred to as "therapeutic agents". The therapeutic agents can be administered via either the oral or parenteral route. Compositions containing both an NK-1 receptor antagonist and a 5HT$_3$ receptor antagonist will generally be administered orally or parenterally daily, in single or divided doses, so that the total amount of each active agent administered falls within the above guidelines.

The therapeutic agents may be administered alone or in combination with pharmaceutically acceptable carriers or diluents by either of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention, when administered separately (i.e., not in the same pharmaceutical composition) are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic agent in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The activity of certain therapeutic agents as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic IC$_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 µg/ml of bacitracin, 4 µg/ml of leupeptin, 2 µg of chymostatin and 200 µ/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the IC$_{50}$ values are calculated by using standard statistical methods.

The activity of certain therapeutic agents as 5HT$_3$ receptor antagonists may be determined by the procedures described by Richardson et al., *Nature*, 316, 126 (1985) and Watling et al., *Eur. J. Pharmacol.*, 149, 397 (1988).

As indicated in Example 1 below, the present inventor has shown that the effectiveness of Compound 1 can be enhanced by a minimally effective dose of ondansetron.

EXAMPLE 1

Adult male ferrets were fasted overnight prior to the experiment. Initially, dose-response relationships were generated for Compound 1 (0.01–1 mg/kg, s.c) and ondansetron (0.003–0.1 mg/kg, s.c.) singly against ipecac at 1 mg/kg, s.c. Compound 1 was injected 30 minutes and 5 minutes prior to the emetogen. Ondansetron was given as a single s.c. injection 30 minutes prior to ipecac. For combination experiments, Compound 1 at 0.01, 0.1 or 0.3 mg/kg and ondansetron at 0.01 mg/kg were both injected s.c. 30 minutes prior to ipecac syrup. A second injection of Compound 1 was given at the same dose as the first 5 minutes prior to the emetogen. Latency to the first retch and the first vomit and number of retching and vomiting episodes were recorded over 60 minutes.

Tables 1 and 2 show the antiemetic effects of Compound 1 and ondansetron given alone. Data have been expressed as (1) the mean latency (in minutes) to first retch or vomit; (2) the mean number of emetic episodes per ferret based on animals that did not exhibit emesis as well as those that did and (3) the mean number of retches/vomits exhibited by animals that remained responsive to ipecac ("responders"). Ferrets that failed to exhibit emesis were omitted from the latter calculation.

TABLE 1

Adult male ferrets were given either Compound 1 (0.01 – 1 mg/kg, s.c.) or vehicle 30 minutes and 5 minutes before ipecac syrup (1 mg/kg, p.o.). Ferrets were then scored for retching and vomiting over 60 minutes. R/T; V/T = number of animals showing retching/vomiting/total number tested. Retches (Vomits) – Mean ± SEM = mean number of retches or vomits per animal (includes zero values from nonresponders). Retches (Vomits) – Responder Mean ± SEM = mean number of retches or vomits per responder (zero values from protected animals were omitted for the calculation).

Effect of Compound 1 on ipecac-induced retching in adult male ferrets

| Treatment | Dose (Mg/Kg) | R/T | Latency To Retch (min) | Retches Mean ± SEM (Range) | Retches Responder Mean ± SEM (Range) |
|---|---|---|---|---|---|
| Saline | | 26/28 | 24.2 ± 1.1 (14–39) | 40.0 ± 5.3 (0–90) | 43.2 ± 5.3 (3–90) |
| Compound 1 | 0.01 | 5/5 | 21.8 ± 2.5 (16–31) | 32.4 ± 8.9 (11–56) | 32.4 ± 8.9 (11–56) |
| | 0.1 | 5/5 | 25.4 ± 1.3 (22–29) | 20.4 ± 5.2 (6–34) | 20.4 ± 5.2 (6–34) |
| | 0.3 | 4/6 | 30.5 ± 3.4 (24–40) | 10.5 ± 4.4* (0–28) | 15.8 ± 4.6 (6–28) |
| | 1.0 | 0/4 | — | 0* | — |

Effect of Compound 1 on ipecac-induced vomiting in adult male ferrets

| Treatment | Dose (Mg/Kg) | V/T | Latency To vomit (min) | Vomits Mean ± SEM (Range) | Retches Responder Mean ± SEM (Range) |
|---|---|---|---|---|---|
| Saline | | 26/28 | 24.9 ± 1.1 (14–39) | 4.5 ± 0.5 (0–10) | 4.8 ± 0.5 (1–10) |
| Compound 1 | 0.01 | 5/5 | 21.8 ± 2.5 (16–31) | 5.0 ± 1.4 (2–10) | 5.0 ± 1.4 (2–10) |
| | 0.1 | 5/5 | 27.0 ± 2.2 (22–34) | 3.2 ± 0.9 (1–6) | 3.2 ± 0.9 (1–6) |
| | 0.3 | 4/6 | 37.0 ± 5.0 (24–48) | 1.8 ± 0.7 (0–4) | 2.8 ± 0.5 (2–4) |
| | 1.0 | 0/4 | — | 0* | — |

*p<0.05 versus the saline group by Dunnett's multiple comparison test.

TABLE 2

Adult male ferrets were given a single injection of ondansetron (0.003 – 0.1 mg/kg, s.c.) or vehicle 30 minutes before ipecac syrup (1 mg/kg, p.o.). Retching and vomiting episodes were then scored over 60 minutes as previously described. R/T; V/T = number of animals showing retching/vomiting/total number tested. Retches (Vomits) – Means ± SEM = mean number of retches or vomits per animal (includes zero values from nonresponders). Retches (Vomits) – Responder Mean ± SEM = mean number of retches or vomits per responder (zero values from protected animals were omitted from the calculation).

Effect of ondansetron on ipecac-induced retching in adult male ferrets

| Treatment | Dose (Mg/Kg) | R/T | Latency To Retch (min) | Retches Mean ± SEM (Range) | Retches Responder Mean ± SEM (Range) |
|---|---|---|---|---|---|
| Saline | | 26/28 | 24.2 ± 1.1 (14–39) | 40.0 ± 5.3 (0–90) | 43.2 ± 5.3 (3–90) |
| Ondansetron | 0.003 | 3/4 | 26.7 ± 3.0 (21–31) | 39.0 ± 18.8 (0–87) | 52.0 ± 19.2 (21–87) |
| | 0.01 | 5/9 | 32.2 ± 3.0 (25–43) | 29.6 ± 11.5 (0–92) | 53.2 ± 12.6 (16–92) |
| | 0.03 | 1/4 | 50 | 6.3 ± 6.3* (0–25) | 25 |
| | 0.1 | 0/4 | — | 0* | — |

Effect of ondansetron on ipecac-induced vomiting in adult male ferrets

| Treatment | Dose (Mg/Kg) | V/T | Latency To vomit (min) | Vomits Mean ± SEM (Range) | Retches Responder Mean ± SEM (Range) |
|---|---|---|---|---|---|
| Saline | | 26/28 | 24.9 ± 1.1 (14–39) | 4.5 ± 0.5 (0–10) | 4.8 ± 0.5 (1–10) |
| Ondansetron | 0.003 | 3/4 | 26.7 ± 3.0 (21–31) | 2.5 ± 1.3 (0–6) | 3.3 ± 1.3 (2–6) |
| | 0.01 | 5/9 | 32.6 ± 2.8 (26–43) | 2.9 ± 1.0 (0–8) | 5.2 ± 0.9 (3–8) |
| | 0.03 | 1/4 | 50 | 0.3 ± 0.3* (0–1) | 1.0 (0–1) |
| | 0.1 | 0/4 | — | 0* | — |

*p<0.05 versus the saline group by Dunnett's multiple comparison test.

TABLE 3

Compound 1 (0.01 – 0.3 mg/kg, s.c) and ondansetron (0.01 mg/kg, s.c.) were co-administered 30 minutes before the emetogen; as in previous studies, a second injection of Compound 1 was given 5 minutes before ipecac syrup (1 mg/kg, p.o.). Retching and vomiting episodes were then counted and means calculated as previously described.

Effect of Compound 1 - Ondansetron combined treatment on ipecac-induced retching in adult male ferrets

| Treatment | Dose (Mg/Kg) | R/T | Latency To Retch (min) | Retches Mean ± SEM (Range) | Retches Responder Mean ± SEM (Range) |
|---|---|---|---|---|---|
| Saline | | 26/28 | 24.2 ± 1.1 (14–39) | 40.0 ± 5.3 (0–90) | 43.2 ± 5.3 (3–90) |
| Compound 1 + Ondansetron | .01/.01 | 6/6 | 31.3 ± 1.2 (27–36) | 28.2 ± 7.2 (7–54) | 28.2 ± 7.2 (7–54) |
| | .1/.01 | 3/5 | 32.7 ± 0.9 (31–34) | 7.0. ± 4.3* (0–23) | 11.7 ± 5.8 (4–23) |
| | .3/.01 | 3/5 | 49.3 ± 5.8 (40–60) | 2.2 ± 1.1* (0–6) | 3.7 ± 1.2* (2–6) |

Effect of Compound 1/Ondansetron combined treatment on ipecac-induced vomiting in adult male ferrets

| Treatment | Dose (Mg/Kg) | V/T | Latency To vomit (min) | Vomits Mean ± SEM (Range) | Retches Responder Mean ± SEM (Range) |
|---|---|---|---|---|---|
| Saline | | 26/28 | 24.9 ± 1.1 (14–39) | 4.5 ± 0.5 (0–10) | 4.8 ± 0.5 (1–10) |
| Compound 1 + Ondansetron | .01/.01 | 5/6 | 34.6 ± 2.6 (27–43) | 2.5 ± 0.8 (0–5) | 3.0 ± 0.7 (1–5) |
| | .1/.01 | 2/5 | 33.5 ± 0.5 (33–34) | 1.2 ± 1.0* (0–5) | 3.0 ± 2.0 (1–5) |
| | .3/.01 | 1/5 | 60 | 0.2 ± 0.2* (0–1) | 1.0 (0–1) |

*$p<0.05$ versus the saline group by Dunnett's multiple comparison test.

Compound 1 decreased the incidence of ipecac-induced retching and vomiting in a dose-dependent manner. All animals exhibited retching and vomiting at doses up to 0.1 mg/kg; Compound 1 blocked both retching and vomiting in 2 of 6 ferrets at 0.3 mg/kg and in 4 of 4 at 1.0 mg/kg. There were no significant increases in the latency to first retch/vomit in this model. Ondansetron, at least at the lower doses, appeared to block retching and vomiting in an "all or none" fashion. For example, ondansetron at 0.003 and 0.01 mg/kg protected 1 of 4 and 4 of 9 ferrets, respectively. Animals that were not completely protected showed the same incidence of retching/vomiting as vehicle-treated animals (Table 2).

Note that in Table 2, ondansetron blocked both retching and vomiting in 4 of 9 ferrets at the 0.01 mg/kg dose. The incidence of emetic episodes in ferrets that were not protected by 0.01 mg/kg ondansetron, however, was similar to that observed in vehicle-treated animals (Mean retches exhibited by responders: Saline=43.2+5.3; 0.01 mg/kg Ondansetron=53.2+12.6). In this small sample, it appeared that when Compound 1 and ondansetron were combined at low doses, Compound 1 tended to mask the "all or none" antiemetic activity of the 5HT$_3$ antagonist (i.e., all of the animals now retched/vomited; see Table 3). The mean number of emetic episodes did tend to be less than that observed in vehicle animals, however. (The difference was not statistically significant.)

Figure 1:
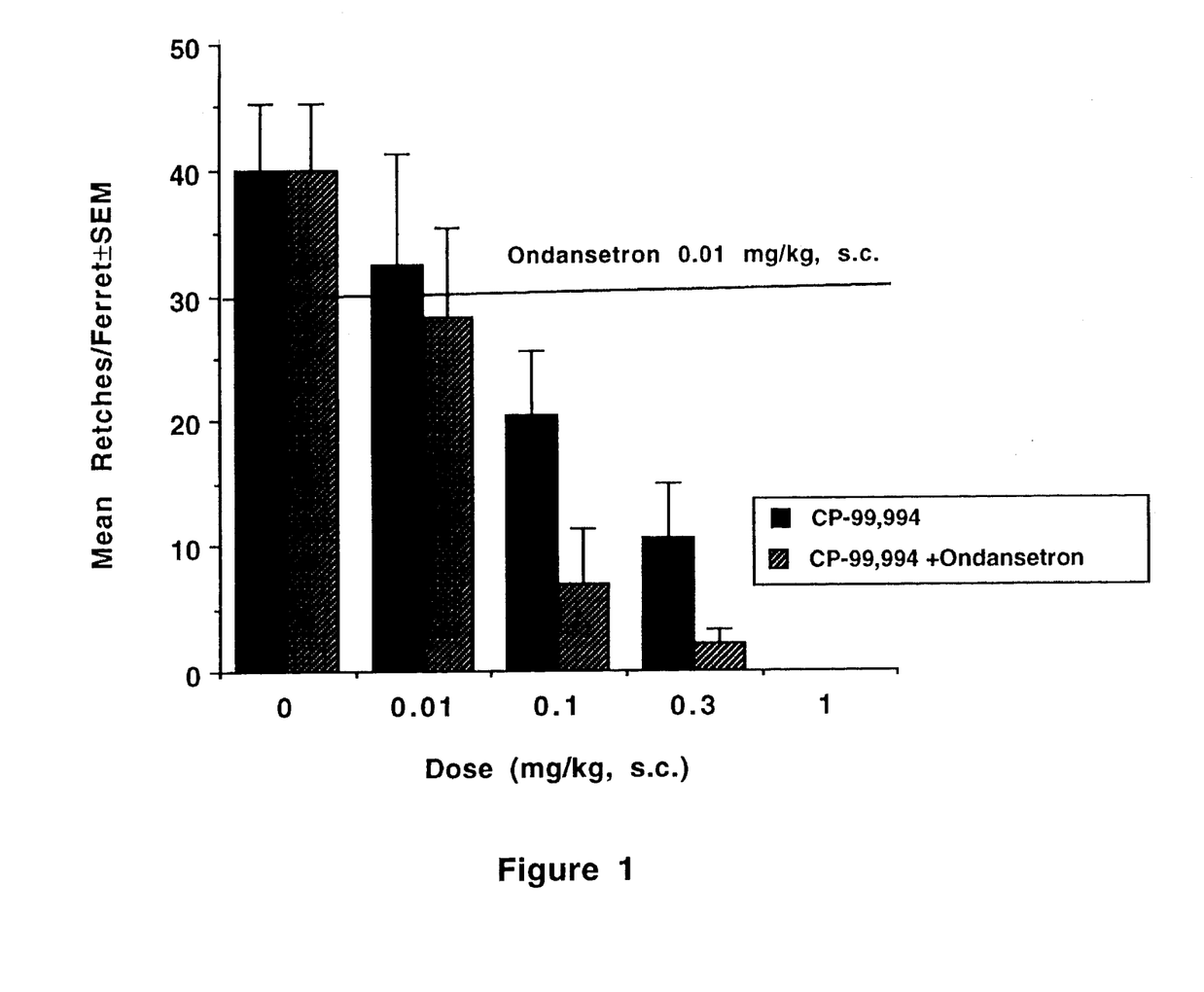
FIG. 1 shows the antiemetic effects of Compound 1 in the absence and presence of 0.01 mg/kg ondansetron. Mean retches/ferret have been calculated using data from all animals tested, as described in Example 1. The horizontal line indicates the mean retches/ferret after ondansetron alone at 0.01 mg/kg.

Data for the Compound 1-ondansetron combination are shown in Table 3. Combining increasing doses of Compound 1 with the 0.01 mg/kg dose of ondansetron decreased the incidence of ipecac-induced emesis compared to Compound 1 alone (see Figure) and increased the number of fully protected animals in a dose-dependent manner. For example, Compound 1, given alone, reduced ipecac-induced retching by 49% at the 0.1 mg/kg and by 74% at the 0.3 mg/kg dose; when combined with 0.01 mg/kg ondansetron, these same two doses of Compound 1 reduced retching by 83% and 95% ($p<0.05$ vs vehicle). When zero values from protected animals were excluded, 0.1 and 0.3 mg/kg Compound 1 decreased the incidence of retching in the remaining ipecac-responsive ferrets by 52.8% and 63%, respectively, when given alone and by 73% and 91% when combined with ondansetron. Combination therapy also appeared to increase the proportion of animals in which vomiting (but not retching) was completely blocked (compare R/T and V/T data in Tables 1 and 3).

I claim:

1. A pharmaceutical composition for the treatment or prevention of emesis comprising a 5HT$_3$ receptor-antagonist, an NK-1 receptor antagonist and a pharmaceutically acceptable carrier.

2. A pharmaceutical composition according to claim 1, wherein the 5HT$_3$ receptor antagonist is selected from ondansetron, tropisetron and granisetron.

3. A pharmaceutical composition according to claim 1, wherein the NK-1 receptor antagonist is selected from the group consisting of:

(2S,3S)-3-(5-tert-butyl-2-methoxybenzyl)amino-2-(3trifluoromethoxyphenyl)piperidine;

(2S,3S)-3-(2-isopropoxy-5-trifluoromethoxybenzyl)amino-2-phenyl-piperidine;

(2S,3S)-3-(2-ethoxy-5-trifluoromethoxybenzyl)amino-2-phenyl-piperidine;
(2S,3S)-3-(2-methoxy-5-trifluoromethoxybenzyl)-amino-2-phenylpiperidine;
(2S,3S)-3(-5-tert-butyl-2-trifluoromethoxybenzyl)amino-2-phenylpiperidine;
2-(diphenylmethyl)-N-(2-methoxy-5-trifluoromethoxy-phenyl)methyl-1-azabicyclo [2.2.2]octan-3-amine;
(2S,3S)-3-[5-chloro-2-(2,2,2-trifluoroethoxy)-benzyl]amino-2-phenylpiperidine;
(2S,3S)-3-(5-tert-butyl-2 -trifluoromethoxybenzyl)amino-2-phenylpiperidine;
(2S,3S)-3-(2-isopropoxy-5-trifluoromethoxybenzyl)amino-2-phenylpiperidine;
(2S,3S) -3-(2-difluoromethoxy-5-trifluoromethoxybenzyl)-amino-2-phenylpiperdine;
(2S,3S)-2-phenyl-3-[2-(2,2,2-trifluoroethoxybenzyl)-aminopiperidine;
(2S,3S)-2-phenyl-3-(2-trifluoromethoxybenzyl)]aminopiperidine;
cis-3-(2-chlorobenzylamino)-2-phenylpiperidine;
cis-3-(2-trifluoromethylbenzylamino)-2-phenyl-piperidine;
cis-3-(2-methoxybenzylamino)-2-(2-fluorophenyl)-piperidine;
cis-3-(2-methoxybenzylamino)-2-(2-chlorophenyl)-piperidine;
cis-3-(2-methoxybenzylamino)-2-(2-methylphenyl)-piperidine;
cis-3-(2-methoxybenzylamino)-2-(3-methoxyphenyl)-piperidine;
cis-3-(2-methoxybenzylamino)-2-(3-fluorophenyl)-piperidine;
cis-3-(2-methoxybenzylamino)-2-(3-chlorophenyl)-piperidine;
cis-3-(2-methoxybenzylamino)-2-phenylpiperidine;
cis-3-(2-methoxybenzylamino)-2-(3-methylphenyl)-piperidine;
cis-3-(2-methoxybenzylamino)-2-(4-fluorophenyl)-piperidine;
cis-3-(2-methoxybenzylamino)-2-(3-thienyl)-piperidine;
cis-3-(2-methoxybenzylamino)-2-phenylazacyclo-heptane;
3-(2-methoxybenzylamino)-4-methyl-2-phenylpiperidine;
3-(2-methoxybenzylamino)-5-methyl-2-phenylpiperidine;
3-(2-methoxybenzylamino)-6-methyl-2-phenylpiperidine;
(2S,3S)-3-(2-methoxybenzylamino)-2-phenylpiperidine;
(2S,3S)-1-(5-carboethoxypent-1-yl)-3-(2-methoxybenzylamino)-2-phenylpiperidine;
(2S,3S)-1-(6-hydroxy-hex-l-yl) -3-(2-methoxybenzylamino)-2-phenylpiperidine;
(2S,3S)-1-(4-hydroxy-4-phenylbut-1-yl)-3-(2-methoxybenzylamino)-2-phenylpiperidine;
(2S,3S)-1-(4-oxo-4-phenylbut-1-yl)-3-(2-methoxybenzylamino)-2-phenylpiperidine;
(2S,3S)-1-(5,6-dihydroxyhex-1-yl)-3-(2-methoxybenzylamino)-2-phenylpiperidine;
cis-3-(5-fluoro-2-methoxybenzylamino)-2-phenyl-piperidine;
(2S,3S)-1-[4-(4-fluorophenyl)-4-oxobut-1-yl]-3-(2-methoxybenzylamino)-2-phenylpiperidine;
(2S,3S)-1-[4-(4-fluorophenyl)-4-hydroxybut-1-yl]-3-(2-methoxybenzylamino) -2-phenylpiperidine;
cis-3-(2-methoxy-5-methylbenzylamino)-2-phenyl-piperidine;
(2S,3S)-1-(4-benzamidobut-1-yl)-3-(2-methoxybenzylamino)-2-phenylpiperidine;
cis-3-(2-methoxynaphth-1-ylmethylamino)-2-phenyl-piperidine;
(2S,3S)-3-(2-methoxybenzylamino)-1-(5-N-methyl-carboxamidopent-1-yl)-2-phenylpiperidine;
(2S,3S)-1-(4-cyanobut-1-yl)-3-(2-methoxybenzylamino)-2-phenylpiperidine;
(2S,3S)-1-[4-(2-naphthamido)but-1-yl]-3-(2-methoxy-benzylamino)-2-phenylpiperidine;
(2S,3S)-1-(5-benzamidopent-1-yl)-3-(2-methoxybenzylamino)-2-phenylpiperidine;
(2S,3S)-1-(5-aminopent-1-yl)-3-(2-methoxybenzylamino)-2-phenylpiperidine;
(2S,3S)-3-(5-chloro-2-methoxybenzylamino)-2-phenyl-piperidine;
(2S,3S)-3-(2,5-dimethoxybenzylamino)-2-phenyl-piperidine;
cis-3-(3,5-difluoro-2-methoxybenzylamino)-2-phenyl-piperidine;
cis-3-(4,5-difluoro-2-methoxybenzylamino)-2-phenyl-piperidine;
cis-3-(2,5-dimethoxybenzylamino)-1-[4-(4-fluorophenyl)-4-oxobut-1-yl]-2-phenylpiperidine;
cis-3-(5-chloro-2-methoxybenzylamino)-1-(5,6-dihydroxyhex-1-yl)-2-phenylpiperidine;
cis-1-(5,6-dihydroxyhex-1-yl)-3-(2,5-dimethoxy-benzylamino)-2-phenylpiperidine;
cis-2-phenyl-3-[-2(prop-2-yloxy)benzylamino]piperidine;
cis-3-(2,5-dimethoxybenzyl)amino-2-(3-methoxy-phenyl)piperidinhydrochloride;
cis-3-(5-chloro-2-methoxybenzyl)amino-2-(3-methoxyphenyl)piperidine dihydrochloride;
cis-3-(5-chloro-2-methoxybenzyl)amino-2-(3-chloro-phenyl)piperidine dihydrochloride;
3-(2-methoxybenzylamino)-2,4-diphenylpiperidine;
cis-3-(2-methoxybenzylamino)-2-phenylpyrrolidine;
(2S,3S)-3-(5-ethyl-2-methoxybenzyl)amino-2-phenyl-piperidine;
(2S,3S)-3-(5-n-butyl-2-methoxybenzyl)amino-2-phenyl-piperidine;
(2S,3S)-3-(2-methoxy-5-n-propylbenzyl)amino-2-phenyl-piperidine;
(2S,3S)-3-(5-isopropyl-2-methoxybenzyl)amino-2-phenyl-piperidine;
(2S,3S)-3-(5-s-butyl-2-methoxybenzyl)amino-2-phenyl-piperidine;
(2S,3S)-3-(5-t-butyl-2-methoxybenzyl)amino-2-phenyl-piperidine;
(2S,3S)-3-(2-methoxy-5-phenylbenzyl)amino-2-phenyl-piperidine;
2,4-dimethylthiazole-5-sulfonic acid [4-methoxy-3-((2,3S)-2-phenylpiperidin-3ylaminomethyl)phenyl]-methylamide;
N-(4,5-dimethylthiazol-2-yl)-N-[4-methoxy-3-((2S,3S)-2-phenylpiperidin-3-ylaminomethyl) phenyl]-methanesulfonamide;
{5-[(4,5-dimethylthiazol-2-yl)methylamino]-2-methoxybenzyl}-((2S,3S)-2-phenylpiperidin-3-yl)amine;
{5-(4,5-dimethylthiazol-2-ylamino)-2-methoxybenzyl}-((2S,3S)-2-phenylpiperidin-3-ylamine;
4,5-dimethylthiazole-2-sulfonic acid methyl-[3-((2S,3S)-2-phenylpiperidin-3-ylaminomethyl)-4-trifluoromethoxyphenyl]-amide;
2,4-dimethylthiazole-5-sulfonic acid [4-isopropoxy-3-((2S,3S)-2-phenylpiperidin -3-ylaminomethyl)phenyl]-methylamide;
2,4-dimethylthiazole-5-sulfonic acid [4-isopropoxy-3-((2S,3S)-2-phenylpiperidin -3-ylaminomethyl)phenyl]-isopropylamide;
2,4-dimethylthiazole-5-sulfonic acid [4-methoxy-3-((2S,3S)-2-phenylpiperidin-3ylaminomethyl)phenyl]-isopropylamide;

2,4-dimethylthiazole-5-sulfonic acid [4-methoxy-3-((2S,3S)-2-phenylpiperidin-3ylaminomethyl]-isobutylamide;
2,4-dimethylthiazole-5-sulfonic acid [4-isopropoxy-3-((2S,3S)-2-phenylpiperidin-3-ylaminomethyl)phenyl]-isobutylamide;
(2S,3S)-N-(5-isopropyl-2-methoxyphenyl)methyl-2-diphenylmethyl-1-azabicyclo [2.2.2]octan-3-amine;
(2S,3S)-N-(5-tert-butyl-2-methoxyphenyl)methyl-2-diphenylmethyl-1-azabicyclo [2.2.2]octan-3-amine;
(2S,3S)-N-(5-methyl-2-methoxyphenyl)methyl-2-diphenylmethyl-1-azabicyclo [2.2.2]octan-3-amine;
(2S,3S)-N-(5-ethyl-2-methoxyphenyl)methyl-2-diphenylmethyl-1-azabicyclo [2.2.2]octan-3-amine;
(2S,3S)-N-(5-isopropyl-2-methoxyphenyl)methyl-2-diphenylmethyl-1-azabicyclo [2.2.2]octan-3-amine;
(2S,3S)-N-(5-sec-butyl-2-methoxyphenyl)methyl-2-diphenylmethyl-1-azabicyclo [2.2.2]octan-3-amine;
(2S,3S)-N-(5-n-propyl-2-methoxyphenyl)methyl-2-diphenylmethyl-1-azabicyclo [2.2.2]octan-3-amine,
(3R,4S,5S,6S)-N,N-diethyl-5-(5-isopropyl-2-methoxy-benzylamino)-6-diphenylmethyl-1-azabicyclo[2.2.2]octane-3-carboxamide;
(3R,4S,5S,6S)-N,N-diethyl-5-(2,5-dimethoxybenzylamino)-6-diphenylmethyl-1-azabicyclo [2.2.2]octane-3-carboxamide;
(3R,4S,5S,6S)-5-(5-isopropyl-2-methoxybenzylamino)-6-diphenylmethyl-1-azabicyclo [2.2.2]octane-3-carboxylic acid;
(3R,4S,5S,6S)-5-(2-methoxy-2-methylthiobenzylamino)-6-diphenylmethyl-1-azabicyclo [2.2.2]octane-3-carboxylic acid;
(3R,4S,5S,6S)-5-(2,5-dimethoxybenzylamino)-6-diphenylmethyl-1-azabicyclo [2.2.2]octane-3-carboxylic acid;
(3R,4S,5S,6S)-5-(2-methoxy-5-methylbenzylamino)-6-diphenylmethyl-1-azabicyclo [2.2.2]octane-3-carboxylic acid;
(3R,4S,5S,6S)-5-(5-ethyl-2-methoxybenzylamino)-6-diphenylmethyl-1-azabicyclo [2.2.2]octane-3-carboxylic acid;
(3R,4S,5S,6S)-5-(2-methoxyl-5-n-propylbenzylamino)-6-diphenylmethyl-1-azabicyclo [2.2.2]octane-3-carboxylic acid;
(3R,4S,5S,6S)-5-(5-sec-butyl-2-methoxybenzylamino)-6-diphenylmethyl-1-azabicyclo [2.2.2]octane-3-carboxylic acid;
(3R,4S,5S,6S)-5-(5-N-methyl-methanesulfonylamino-2-methoxy-benzylamino)-6-diphenylmethyl-1-azabicyclo [2.2.2]octane-3-carboxylic acid;
(3R,4S,5S,6S)-5-(2-methoxy-5-methylsulfinylbenzylamino)-6-diphenylmethyl-1-azabicyclo[2.2.2]octane-3-carboxylic acid;
(3R,4S,5S,6S)-5-(2-methoxy-5-trifluoromethoxybenzylamino)-6-diphenylmethyl-1-azabicyclo[2.2.2]octane-3-carboxylic acid;
(3R,4S,5S,6S)-5-(2-methoxy-5-methylsulfonylbenzylamino)-6-diphenylmethyl-1-azabicyclo[2.2.2]octane-3-carboxylic acid;
(3R,4S,5S,6S)-5-(5-dimethylamino-2-methoxybenzylamino)-6-diphenylmethyl-1-azabicyclo[2.2.2]octane-3-carboxylic acid;
(3R,4S,5S,6S)-5-(5-isopropyl-2-methoxybenzylamino)-6-diphenylmethyl-1-azabicyclo[2.2.2]octane-2-carboxylic acid;
(3R,4S,5S,6S)-5-(2-methoxy-5-methylthiobenzylamino)-6-diphenylmethyl-1-azabicyclo [2.2.2]octane-2-carboxylic acid;
(3R,4S,5S,6S)-5-(2,5-dimethoxybenzylamino)-6-diphenylmethyl-1-azabicyclo [2.2.2]octane-2-carboxylic acid;
(3R,4S,5S,6S)-5-(2-methoxy-5-methylbenzylamino)-6-diphenylmethyl-1-azabicyclo [2.2.2]octane-2-carboxylic acid;
(3R,4S,5S,6S)-5-(5-ethyl-2-methoxybenzylamino)-6-diphenylmethyl-1-azabicyclo [2.2.2]octane-2-carboxylic acid;
(3R,4S,5S,6S)-5-(2-methoxyl-5-n-propylbenzylamino)-6-diphenylmethyl-1-azabicyclo [2.2.2]octane-2-carboxylic acid;
(3R,4S,5S,6S)-5-(5-sec-butyl-2-methoxybenzylamino)-6-diphenylmethyl-1-azabicyclo [2.2.2]octane-2-carboxylic acid;
(3R,4S,5S,6S)-5-(5-N-methyl-methanesulfonylamino-2-methoxybenzyl-amino)-6-diphenylmethyl-1-azabicyclo [2.2.2]octane-2-carboxylic acid;
(3R,4S,5S,6S)-5-(2-methoxy-5-methylsulfinylbenzyl-amino)-6-diphenylmethyl-1-azabicyclo[2.2.2]octane-2-carboxylic acid;
(3R,4S,5S,6S)-5-(2-methoxy-5-trifluoromethoxybenzyl-amino)-6-diphenylmethyl-1-azabicyclo-[2.2.2]octane-2-carboxylic acid;
(3R,4S,5S,6S)-5-(2-methoxy-5-methylsulfonylbenzyl-amino)-6-diphenylmethyl-1-azabicyclo[2.2.2]octane-2-carboxylic acid; and
(3R,4S,5S,6S)-5-(5-dimethylamino-2-methoxybenzyl-amino)-6-diphenylmethyl-1-azabicyclo [2.2.2]octane-2-carboxylic acid;
and the pharmaceutically acceptable salts of the foregoing compounds.

4. A method of treating or preventing emesis in a mammal, comprising administering to said mammal an antiemetic effective amount of a pharmaceutical composition comprising a 5HT$_3$ receptor antagonist, an NK-1 receptor antagonist and a pharmaceutically acceptable carrier.

5. A method according to claim 4, wherein the combination of the 5HT$_3$ receptor antagonist and the NK-1 receptor antagonist is used to treat or prevent ondansetron-resistant emesis.

6. A method of treating ore preventing emesis in a mammal, comprising administering to said mammal an antiemetic effective amount of a pharmaceutical composition comprising an NK-1 receptor antagonist and either ondansetron, tropisetron or granisetron.

7. A method of treating or preventing emesis in a mammal, comprising administering to said mammal a 5HT$_3$ receptor antagonist and an NK-1 receptor antagonist in amounts that render the combination of such two active agents effective in the treatment or prevention of such disorder.

8. A method according to claim 7 wherein the NK-1 receptor antagonist is selected from the group consisting of:
(2S,3S)-3-(5-tert-butyl-2-methoxybenzyl)amino-2-(3-trifluoromethoxyphenyl)piperidine;
(2S,3S)-3-(2-isopropoxy-5-trifluoromethoxybenzyl)amino-2-phenyl-piperidine;
(2S,3S)-3-(2-ethoxy-5-trifluoromethoxybenzyl)amino-2-phenyl-piperidine;
(2S,3S)-3-(2-methoxy-5-trifluoromethoxybenzyl)-amino-2-phenylpiperidine;
(2S,3S)-3(-5-tert-butyl-2-trifluoromethoxybenzyl)amino-2-phenylpiperidine;
2-(diphenylmethyl)-N-(2-methoxy-5-trifluoromethoxy-phenyl)methyl-1-azabicyclo [2.2.2]octan-3-amine;
(2S,3S)-3-[5-chloro-2-(2,2,2-trifluoroethoxy)-benzyl] amino-2-phenylpiperidine;
(2S,3S)-3-(5-tert-butyl-2-trifluoromethoxybenzyl)amino-2-phenylpiperidine;
(2S,3S)-3-(2-isopropoxy-5-trifluoromethoxybenzyl)amino-2-phenylpiperidine;

(2S,3S)-3-(2-difluoromethoxy-5-trifluoromethoxybenzyl)-amino-2-phenylpiperidine;
(2S,3S)-2-phenyl-3-[2-(2,2,2-trifluoroethoxybenzyl)-aminopiperidine;
(2S,3S)-2-phenyl-3-(2-trifluoromethoxybenzyl)]aminopiperidine;
cis-3-(2-chlorobenzylamino)-2-phenylpiperidine;
cis-3-(2-trifluoromethylbenzylamino)-2-phenyl-piperidine;
cis-3-(2-methoxybenzylamino)-2-(2-fluorophenyl)-piperidine;
cis-3-(2-methoxybenzylamino)-2-(2-chlorophenyl)-piperidine;
cis-3-(2-methoxybenzylamino)-2-(2-methylphenyl)-piperidine;
cis-3-(2-methoxybenzylamino)-2-(3-methoxyphenyl)-piperidine;
cis-3-(2-methoxybenzylamino)-2-(3-fluorophenyl)-piperidine;
cis-3-(2-methoxybenzylamino)-2-(3-chlorophenyl)-piperidine;
cis-3-(2-methoxybenzylamino)-2-phenylpiperidine;
cis-3-(2-methoxybenzylamino)-2-(3-methylphenyl)-piperidine;
cis-3-(2-methoxybenzylamino)-2-(4-fluorophenyl)-piperidine;
cis-3-(2-methoxybenzylamino)-2-(3-thienyl)-piperidine;
cis-3-(2-methoxybenzylamino)-2-phenylazacyclo-heptane;
3-(2-methoxybenzylamino)-4-methyl-2-phenylpiperidine;
3-(2-methoxybenzylamino)-5-methyl-2-phenylpiperidine;
3-(2-methoxybenzylamino)-6-methyl-2-phenylpiperidine;
(2S,3S)-3-(2-methoxybenzylamino)-2-phenylpiperidine;
(2S,3S)-1-(5-carboethoxypent-1-yl)-3-(2-methoxybenzylamino)-2-phenylpiperidine;
(2S,3S)-1-(6-hydroxy-hex-l-yl)-3-(2-methoxybenzylamino)-2-phenylpiperidine;
(2S,3S)-1-(4-hydroxy-4-phenylbut-1-yl)-3-(2-methoxybenzylamino)-2-phenylpiperidine;
(2S,3S)-1-(4-oxo-4-phenylbut-1-yl)-3-(2-methoxybenzylamino)-2-phenylpiperidine;
(2S,3S)-1-(5,6-dihydroxyhex-1-yl)-3-(2-methoxybenzylamino)-2-phenylpiperidine;
cis-3-(5-fluoro-2-methoxybenzylamino)-2-phenyl-piperidine;
(2S,3S)-1-[4-(4-fluorophenyl)-4-oxobut-1-yl]-3-(2-methoxybenzylamino)-2-phenylpiperidine;
(2S,3S)-1-[4-[4-fluorophenyl)-4-hydroxybut-1-yl]-3-(2-phenylpiperidine;
cis-3-(2-methoxy-5-methylbenzylamino)-2-phenyl-piperidine;
(2S,3S)-1-(4-benzamidobut-1-yl)-3-(2-methoxybenzylamino)-2-phenylpiperidine;
cis-3-(2-methoxynaphth-1-ylmethylamino)-2-phenyl-piperidine;
(2S,3S)-3-(2-methoxybenzylamino)-1-(5-N-methyl-carboxamidopent-1-yl)-2-phenylpiperidine;
(2S,3S)-1-(4-cyanobut-1-yl)-3-(2-methoxybenzylamino)-2-phenylpiperidine;
(2S,3S)-1-[4-(2-naphthamido)but-1-yl]-3-(2-methoxy-benzylamino)-2-phenylpiperidine;
(2S,3S)-1-(5-benzamidopent-1-yl)-3-(2-methoxybenzylamino)-2-phenylpiperidine;
(2S,3S)-1-(5-aminopent-1-yl)-3-(2-methoxybenzylamino)-2-phenylpiperidine;
(2S,3S)-3-(5-chloro-2-methoxybenzylamino)-2-phenyl-piperidine;
(2S,3S)-3-(2,5-dimethoxybenzylamino)-2-phenyl-piperidine;
cis-3-(3,5-difluoro-2-methoxybenzylamino)-2-phenyl-piperidine;
cis-3-(4,5-difluoro-2-methoxybenzylamino)-2-phenyl-piperidine;
cis-3-(2,5-dimethoxybenzylamino)-1-[4-(4-fluorophenyl)-4-oxobut-1-yl]-2-phenylpiperidine;
cis-3-(5-chloro-2-methoxybenzylamino)-1-(5,6-dihydroxy-hex-1-yl)-2-phenylpiperidine;
cis-1-(5,6-dihydroxyhex-1-yl)-3-(2,5-dimethoxy-benzylamino)-2-phenylpiperidine;
cis-2-phenyl-3-[-2(prop-2-yloxy)benzylamino]piperidine;
cis-3-(2,5-dimethoxybenzyl)amino-2-(3-methoxy-phenyl)piperidinhydrochloride;
cis-3-(5-chloro-2-methoxybenzyl)amino-2-(3-methoxyphenyl)piperidine dihydrochloride;
cis-3-(5-chloro-2-methoxybenzyl)amino-2-(3-chloro-phenyl)piperidine dihydrochloride;
3-(2-methoxybenzylamino)-2,4-diphenylpiperidine;
cis-3-(2-methoxybenzylamino)-2-phenylpyrrolidine;
(2S,3S)-3-(5-ethyl-2-methoxybenzyl)amino-2-phenyl-piperidine;
(2S,3S)-3-(5-n-butyl-2-methoxybenzyl)amino-2-phenyl-piperidine;
(2S,3S)-3-(2-methoxy-5-n-propylbenzyl)amino-2-phenyl-piperidine;
(2S,3S)-3-(5-isopropyl-2-methoxybenzyl)amino-2-phenyl-piperidine;
(2S,3S)-3-(5-s-butyl-2-methoxybenzyl)amino-2-phenyl-piperidine;
(2S,3S)-3-(5-t-butyl-2-methoxybenzyl)amino-2-phenyl-piperidine;
(2S,3S)-3-(2-methoxy-5-phenylbenzyl)amino-2-phenyl-piperidine;
2,4-dimethylthiazole-5-sulfonic acid [4-methoxy-3-((2,3S)-2-phenylpiperidin-3-ylaminomethyl)phenyl]-methylamide;
N-(4,5-dimethylthiazol-2-yl)-N-[4-methoxy-3-((2S,3S)-2-phenylpiperidin-3-ylaminomethyl) phenyl]-methanesulfonamide;
{5-[(4,5-dimethylthiazol-2-yl)methylamino]-2-methoxybenzyl}-((2S,3S)-2-phenylpiperidin -3-yl)amine;
{5-(4,5-dimethylthiazol-2-ylamino)-2-methoxybenzyl}-((2S,3S)-2-phenylpiperidin -3-ylamine;
4,5-dimethylthiazole-2-sulfonic acid methyl-[3-((2S,3S)-2-phenylpiperidin-3-ylaminomethyl)-4-trifluoromethoxyphenyl]-amide;
2,4-dimethylthiazole-5-sulfonic acid [4-isopropoxy-3-((2S,3S)-2-phenylpiperidin -3-ylaminomethyl)phenyl]-methylamide;
2,4-dimethylthiazole-5-sulfonic acid [4-isopropoxy-3-((2S,3S)-2-phenylpiperidin -3-ylaminomethyl)phenyl]-isopropylamide;
2,4-dimethylthiazole-5-sulfonic acid [4-methoxy-3-((2S,3S)-2-phenylpiperidin-3-ylaminomethyl)phenyl]-isopropylamide;
2,4-dimethylthiazole-5-sulfonic acid [4-methoxy-3-((2S,3S)-2-phenylpiperidin-3-ylaminomethyl)phenyl]-isobutylamide;
2,4-dimethylthiazole-5-sulfonic acid [4-isopropoxy-3-((2S,3S)-2-phenylpiperidin-3-ylaminomethyl)phenyl]-isobutylamide;
(2S,3S)-N-(5-isopropyl-2-methoxyphenyl)methyl-2-diphenylmethyl-1-azabicyclo -2.2.2]octan-3-amine;
(2S,3S)-N-(5-tert-butyl-2-methoxyphenyl)methyl-2-diphenylmethyl-1-azabicyclo [2.2.2]octan-3-amine;
(2S,3S)-N-(5-methyl-2-methoxyphenyl)methyl-2-diphenylmethyl-1-azabicyclo [2.2.2]octan-3-amine;

(2S,3S)-N-(5-ethyl-2-methoxyphenyl)methyl-2-diphenylmethyl-1-azabicyclo [2.2.2]octan-3-amine;
(2S,3S)-N-(5-isopropyl-2-methoxyphenyl)methyl-2-diphenylmethyl-1-azabicyclo[2.2.2]octan-3-amine;
(2S,3S)-N-(5-sec-butyl-2-methoxyphenyl)methyl-2-diphenylmethyl-1-azabicyclo [2.2.2]octan-3-amine;
(2S,3S)-N-(5-n-propyl-2-methoxyphenyl)methyl-2-diphenylmethyl-1-azabicyclo [2.2.2]octan-3-amine,
(3R,4S,5S,6S)-N,N-diethyl-5-(5-isopropyl-2-methoxy-benzylamino)-6-diphenylmethyl -1-azabicyclo[2.2.2]octane-3-carboxamide;
(3R,4S,5S,6S)-N,N-diethyl-5-(2,5-dimethoxybenzylamino)-6-diphenylmethyl-1-azabicyclo [2.2.2]octane-3-carboxamide;
(3R,4S,5S,6S)-5-(5-isopropyl-2-methoxybenzylamino)-6-diphenylmethyl-1-azabicyclo [2.2.2]octane-3-carboxylic acid;
(3R,4S,5S,6S)-5-(2-methoxy-2-methylthiobenzylamino)-6-diphenylmethyl-1-azabicyclo [2.2.2]octane-3-carboxylic acid;
(3R,4S,5S,6S)-5-(2,5-dimethoxybenzylamino)-6-diphenylmethyl-1-azabicyclo [2.2.2]octane-3-carboxylic acid;
(3R,4S,5S,6S)-5-(2-methoxy-5-methylbenzylamino)-6-diphenylmethyl-1-azabicyclo [2.2.2]octane-3-carboxylic acid;
(3R,4S,5S,6S)-5-(5-ethyl-2-methoxybenzylamino)-6-diphenylmethyl-1-azabicyclo [2.2.2]octane-3-carboxylic acid;
(3R,4S,5S,6S)-5-(2-methoxyl-5-n-propylbenzylamino)-6-diphenylmethyl-1-azabicyclo [2.2.2]octane-3-carboxylic acid;
(3R,4S,5S,6S)-5-(5-sec-butyl-2-methoxybenzylamino)-6-diphenylmethyl-1-azabicyclo [2.2.2]octane-3-carboxylic acid;
(3R,4S,5S,6S)-5-(5-N-methyl-methanesulfonylamino-2-methoxy-benzylamino)-6-diphenylmethyl-1-azabicyclo [2.2.2]octane-3-carboxylic acid;
(3R,4S,5S,6S)-5-(2-methoxy-5-methylsulfinylbenzyl-amino)-6-diphenylmethyl-1-azabicyclo[2.2.2]octane-3-carboxylic acid;
(3R,4S,5S,6S)-5-(2-methoxy-5-trifluoromethoxybenzyl-amino)-6-diphenylmethyl-1-azabicyclo[2.2.2]octane-3-carboxylic acid;
(3R,4S,5S,6S)-5-(2-methoxy-5-methylsulfonylbenzyl-amino)-6-diphenylmethyl-1-azabicyclo[2.2.2]octane-3-carboxylic acid;
(3R,4S,5S,6S)-5-(5-dimethylamino-2-methoxybenzylamino)-6-diphenylmethyl-1-azabicyclo [2.2.2]octane-3-carboxylic acid;
(3R,4S,5S,6S)-5-(5-isopropyl-2-methoxybenzylamino)-6-diphenylmethyl-1-azabicyclo [2.2.2]octane-2-carboxylic acid;
(3R,4S,5S,6S)-5-(2-methoxy-5-methylthiobenzylamino)-6-diphenylmethyl-1-azabicyclo [2.2.2]octane-2-carboxylic acid;
(3R,4S,5S,6S)-5-(2,5-dimethoxybenzylamino)-6-diphenylmethyl-1-azabicyclo [2.2.2]octane-2-carboxylic acid;
(3R,4S,5S,6S)-5-(2-methoxy-5-methylbenzylamino)-6-diphenylmethyl-1-azabicyclo [2.2.2]octane-2-carboxylic acid;
(3R,4S,5S,6S)-5-(5-ethyl-2-methoxybenzylamino)-6-diphenylmethyl-1-azabicyclo [2.2.2]octane-2-carboxylic acid;
(3R,4S,5S,6S)-5-(2-methoxyl-5-n-propylbenzylamino)-6-diphenylmethyl-1-azabicyclo [2.2.2]octane-2-carboxylic acid;
(3R,4S,5S,6S)-5-(5-sec-butyl-2-methoxybenzylamino)-6-diphenylmethyl-1-azabicyclo [2.2.2]octane-2-carboxylic acid;
(3R,4S,5S,6S)-5-(5-N-methyl-methanesulfonylamino-2-methoxybenzyl-amino)-6-diphenylmethyl-1-azabicyclo [2.2.2]octane-2-carboxylic acid;
(3R,4S,5S,6S)-5-(2-methoxy-5-methylsulfinylbenzyl-amino)-6-diphenylmethyl-1-azabicyclo[2.2.2]octane-2-carboxylic acid;
(3R,4S,5S,6S)-5-(2-methoxy-5-trifluoromethoxybenzyl-amino)-6-diphenylmethyl-1-azabicyclo[2.2.2]octane-2-carboxylic acid;
(3R,4S,5S,6S)-5-(2-methoxy-5-methylsulfonylbenzyl-amino)-6-diphenylmethyl-1-azabicyclo[2.2.2]octane-2-carboxylic acid; and
(3R,4S,5S,6S)-5-(5-dimethylamino-2-methoxybenzylamino)-6-diphenylmethyl-1-azabicyclo[2.2.2]octane-2-carboxylic acid;
and the pharmaceutically acceptable salts of the foregoing compounds.

9. A method according to claim 7, wherein the combination of the 5HT$_3$ receptor antagonist and the NK-1 receptor antagonist is used to treat or prevent ondansetron-resistant emesis.

10. A method according to claim 7, wherein the NK-1 receptor antagonist is administered in an amount from about 0.36 to about 4.3 mg per kg body weight of the subject being treated per day and the 5HT$_3$ receptor antagonist is administered in an amount from about 0.007 to about 0.07 mg per kg body weight of the subject being treated per day.

11. A method according to claim 7 wherein the 5HT$_3$ antagonist is selected from ondansetron, granisetron and tropisetron.

12. A method according to claim 7, wherein the 5HT$_3$ receptor antagonist and the NK-1 receptor antagonist are administered separately according to a dose regimen that renders the combination of the separately administered active agents effective in the treatment or prevention of emesis.

13. A method according to claim 12, wherein the combination of the 5HT$_3$ receptor antagonist and the NK-1 receptor antagonist is used to treat or prevent ondansetron-resistant emesis.

14. A method of treating or preventing emesis in mammal, comprising administering to said mammal an antiemetic effective amount of a pharmaceutical composition comprising a 5HT$_3$ receptor antagonist and a compound selected from the following:
(2S,3S) -3-(5-tert-butyl-2-methoxybenzyl)amino-2-(3-trifluoromethoxyphenyl)piperidine;
(2S,3S) -3-(2-isopropoxy-5-trifluoromethoxybenzyl)amino -2phenyl-piperidine;
(2S,3S) -3-(2-ethoxy-5-trifluoromethoxybenzyl)amino-2-phenyl-piperidine;
(2S,3S) -3-(2-methoxy-5-trifluoromethoxybenzyl)-amino-2-phenylpiperidine;
(2S,3S) -3(-5-tert-butyl-2-trifluoromethoxybenzyl)amino -2-phenylpiperidine;
2-(diphenylmethyl) -N-(2-methoxy-5-trifluoromethoxyphenyl) methyl-1-azabicyclo[2.2.2]octan-3-amine;
(2S,3S) -3-[5-chloro-2-(2,2,2-trifluoroethoxy)benzyl] amino-2-phenylpiperidine;
(2S,3S)-3-(5-tert-butyl-2-trifluoromethoxybenzyl)amino -2-phenylpiperidine;
(2S,3S) -3-(2-isopropoxy-5-trifluoromethoxybenzyl)amino -2-phenylpiperidine;
(2S,3S) -3-(2-difluoromethoxy-5-trifluoromethoxybenzyl) -amino-2-phenylpiperidine;
(2S,3S) -2-phenyl-3-[2-(2,2,2-trifluoroethoxybenzyl)aminopiperidine;

(2S,3S)-2-phenyl-3-(2-trifluoromethoxybenzyl)]aminopiperidine;
cis-3-(2-chlorobenzylamino)-2-phenylpiperidine;
cis-3-(2-trifluoromethylbenzylamino)-2-phenyl-piperidine;
cis-3-(2-methoxybenzylamino)-2-(2-fluorophenyl)-piperidine;
cis-3-(2-methoxybenzylamino)-2-(2-chlorophenyl)-piperidine;
cis-3-(2-methoxybenzylamino)-2-(2-methylphenyl)-piperidine;
cis-3-(2-methoxybenzylamino)-2-(3-methoxyphenyl)-piperidine;
cis-3-(2-methoxybenzylamino)-2-(3-fluorophenyl)-piperidine;
cis-3-(2-methoxybenzylamino)-2-(3-chlorophenyl)-piperidine;
cis-3-(2-methoxybenzylamino)-2-phenylpiperidine;
cis-3-(2-methoxybenzylamino)-2-(3-methylphenyl)-piperidine;
cis-3-(2-methoxybenzylamino)-2-(4-fluorophenyl)-piperidine;
cis-3-(2-methoxybenzylamino)-2-(3-thienyl)-piperidine;
cis-3-(2-methoxybenzylamino)-2-phenylazacyclo-heptane;
3-(2-methoxybenzylamino)-4-methyl-2-phenylpiperidine;
3-(2-methoxybenzylamino)-5-methyl-2-phenylpiperidine;
3-(2-methoxybenzylamino)-6-methyl-2-phenylpiperidine;
(2S,3S)-3-(2-methoxybenzylamino)-2-phenylpiperidine;
(2S,3S)-1-(5-carboethoxypent-1-yl)-3-(2-methoxybenzylamino)-2-phenylpiperidine;
(2S,3S)-1-(6-hydroxy-hex-l-yl)-3-(2-methoxybenzylamino)-2-phenylpiperidine;
(2S,3S)-1-(4-hydroxy-4-phenylbut-1-yl)-3-(2-methoxybenzylamino)-2-phenylpiperidine;
(2S,3S)-1-(4-oxo-4-phenylbut-1-yl)-3-(2-methoxybenzylamino)-2-phenylpiperidine;
(2S,3S)-1-(5,6-dihydroxyhex-1-yl)-3-(2-methoxybenzylamino)-2-phenylpiperidine;
cis-3-(5-fluoro-2-methoxybenzylamino)-2-phenylpiperidine;
(2S,3S)-1-[4-(4-fluorophenyl)-4-oxobut-1-yl]-3-(2-methoxybenzylamino)-2-phenylpiperidine;
(2S,3S)-1-[4-(4-fluorophenyl)-4-hydroxybut-1-yl]-3-(2-methoxybenzylamino)-2-phenylpiperidine;
cis-3-(2-methoxy-5-methylbenzylamino)-2-phenylpiperidine;
(2S,3S)-1-(4-benzamidobut-1-yl)-3-(2-methoxybenzylamino)-2-phenylpiperidine;
cis-3-(2-methoxynaphth-1-ylmethylamino)-2-phenylpiperidine;
(2S,3S)-3-(2-methoxybenzylamino)-1-(5-N-methylcarboxamidopent-1-yl)-2-phenylpiperidine;
(2S,3S)-1-(4-cyanobut-1-yl)-3-(2-methoxybenzylamino)-2phenylpiperidine;
(2S,3S)-1-[4-(2-naphthamido)but-1-yl]-3-(2-methoxybenzylamino)-2-phenylpiperidine;
(2S,3S)-1-(5-benzamidopent-1-yl)-3-(2-methoxybenzylamino)-2-phenylpiperidine;
(2S,3S)-1-(5-aminopent-1-yl)-3-(2-methoxybenzylamino)-2-phenylpiperidine;
(2S,3S)-3-(5-chloro-2-methoxybenzylamino)-2-phenylpiperidine;
(2S,3S)-3-(2,5-dimethoxybenzylamino)-2-phenylpiperidine;
cis-3-(3,5-difluoro-2-methoxybenzylamino)-2-phenylpiperidine;
cis-3-(4,5-difluoro-2-methoxybenzylamino)-2-phenylpiperidine;
cis-3-(2,5-dimethoxybenzylamino)-1-[4-(4-fluorophenyl)-4-oxobut-1-yl]-2-phenylpiperidine;
cis-3-(5-chloro-2-methoxybenzylamino)-1-(5,6-dihydroxyhex-1-yl)-2-phenylpiperidine;
cis-1-(5,6-dihydroxyhex-1-yl)-3-(2,5-dimethoxybenzylamino)-2-phenylpiperidine;
cis-2-phenyl-3-[-2(prop-2-yloxy)benzylamino]piperidine;
cis-3-(2,5-dimethoxybenzyl)amino-2-(3-methoxyphenyl)piperidine hydrochloride;
cis-3-(5-chloro-2-methoxybenzyl)amino-2-(3-methoxyphenyl)piperidine dihydrochloride;
cis-3-(5-chloro-2-methoxybenzyl)amino-2-(3-chlorophenyl)piperidine dihydrochloride;
3-(2-methoxybenzylamino)-2,4-diphenylpiperidine;
cis-3-(2-methoxybenzylamino)-2-phenylpyrrolidine;
(2S,3S)-3-(5-ethyl-2-methoxybenzyl)amino-2-phenylpiperidine;
(2S,3S)-3-(5-n-butyl-2-methoxybenzyl)amino-2-phenylpiperidine;
(2S,3S)-3-(2-methoxy-5-n-propylbenzyl)amino-2-phenylpiperidine;
(2S,3S)-3-(5-isopropyl-2-methoxybenzyl)amino-2-phenylpiperidine;
(2S,3S)-3-(5-s-butyl-2-methoxybenzyl)amino-2-phenylpiperidine;
(2S,3S)-3-(5-t-butyl-2-methoxybenzyl)amino-2-phenylpiperidine;
(2S,3S)-3-(2-methoxy-5-phenylbenzyl)amino-2-phenylpiperidine;
2,4-dimethylthiazole-5-sulfonic acid [4-methoxy-3((2S,3S)-2-phenylpiperidin-3-ylaminomethyl)phenyl]methylamide;
N-(4,5-dimethylthiazol-2-yl)-N-[4-methoxy-3-((2S,3S)-2-phenylpiperidin-3-yl-aminomethyl) phenyl]-methanesulfonamide;
{5-[(4,5-dimethylthiazol-2-yl)methylamino]-2-methoxybenzyl}-((2S,3S)-2-phenylpiperidin-3-yl)amine;
{5-(4,5-dimethylthiazol-2-ylamino)-2-methoxybenzyl}-((2S,3S)-2-phenylpiperidin-3-ylamine;
4,5-dimethylthiazole-2-sulfonic acid methyl-[3-((2S,3S)-2-phenylpiperidin-3-ylaminomethyl)-4-trifluoromethoxyphenyl]amide;
2,4-dimethylthiazole-5-sulfonic acid [4-isopropoxy-3-((2S,3S)-2-phenylpiperidin-3-ylaminomethyl)phenyl]-methylamide;
2,4-dimethylthiazole-5-sulfonic acid [4-isopropoxy-3-((2S,3S)-2-phenylpiperidin-3-ylaminomethyl)phenyl]-isopropylamide;
2,4-dimethylthiazole-5-sulfonic acid [4-methoxy-3-((2S,3S)-2-phenylpiperidin-3-ylaminomethyl)phenyl]isopropylamide;
2,4-dimethylthiazole-5-sulfonic acid [4-methoxy-3-((2S,3S)-2-phenylpiperidin-3-ylaminomethyl)phenyl]isobutylamide;
2,4-dimethylthiazole-5-sulfonic acid [4-isopropoxy-3-((2S,3S)-2-phenylpiperidin-3-ylaminomethyl)phenyl]-isobutylamide;
(2S,3S)-N-(5-isopropyl-2-methoxyphenyl)methyl-2-diphenylmethyl-1-azabicyclo[2.2.2]octan-3-amine;
(2S,3S)-N-(5-tert-butyl-2-methoxyphenyl)methyl-2-diphenylmethyl-1-azabicyclo[2.2.2]octan-3-amine;
(2S,3S)-N-(5-methyl-2-methoxyphenyl)methyl-2-diphenylmethyl-1-azabicyclo[2.2.2]octan-3-amine;
(2S,3S)-N-(5-ethyl-2-methoxyphenyl)methyl-2-diphenylmethyl-1-azabicyclo[2.2.2]octan-3-amine;
(2S,3S)-N-(5-isopropyl-2-methoxyphenyl)methyl-2-diphenylmethyl-1-azabicyclo[2.2.2]octan-3-amine;

(2S,3S)-N-(5-sec-butyl-2-methoxyphenyl)methyl-2-diphenylmethyl-1-azabicyclo[2.2.2]octan-3-amine;

(2S,3S)-N-(5-n-propyl-2-methoxyphenyl)methyl-2-diphenylmethyl-1-azabicyclo[2.2.2]octan-3-amine, (3R,4S,5S,6S)-N,N-diethyl-5-(5-isopropyl-2-methoxybenzylamino)-6-diphenylmethyl-1-azabicyclo[2.2.2]octane-3-carboxamide;

(3R,4S,5S,6S)-N,N-diethyl-5-(2,5-dimethoxybenzylamino)-6-diphenylmethyl-1-azabicyclo[2.2.2]octane-3-carboxamide;

(3R,4S,5S,6S)-5-(5-isopropyl-2-methoxybenzylamino)-6-diphenylmethyl-1-azabicyclo[2.2.2]octane-3-carboxylic acid;

(3R,4S,5S,6S)-5-(2-methoxy-2-methylthiobenzylamino)-6-diphenylmethyl-1-azabicyclo[2.2.2]octane-3-carboxylic acid;

(3R,4S,5S,6S)-5-(2,5-dimethoxybenzylamino)-6-diphenylmethyl-1-azabicyclo-[2.2.2]octane-3-carboxylic acid;

(3R,4S,5S,6S)-5-(2-methoxy-5-methylbenzylamino)-6-diphenylmethyl-1-azabicyclo[2.2.2]octane-3-carboxylic acid;

(3R,4S,5S,6S)-5-(5-ethyl-2-methoxybenzylamino)-6-diphenylmethyl-1-azabicyclo[2.2.2]octane-3-carboxylic acid;

(3R,4S,5S,6S)-5-(2-methoxyl-5-n-propylbenzylamino)-6-diphenylmethyl-1-azabicyclo[2.2.2]octane-3-carboxylic acid;

(3R,4S,5S,6S)-5-(5-sec-butyl-2-methoxybenzylamino)-6-diphenylmethyl-1-azabicyclo[2.2.2]octane-3-carboxylic acid;

(3R,4S,5S,6S)-5-(5-N-methyl-methanesulfonylamino-2-methoxy-benzylamino)-6-diphenylmethyl-1-azabicyclo[2.2.2]octane-3-carboxylic acid;

(3R,4S,5S,6S)-5-(2-methoxy-5-methylsulfinylbenzylamino) -6-diphenylmethyl-1-azabicyclo[2.2.2]octane-3carboxylic acid;

(3R,4S,5S,6S)-5-(2-methoxy-5-trifluoromethoxybenzylamino) -6-diphenylmethyl-1-azabicyclo[2.2.2]octane-3carboxylic acid;

(3R,4S,5S,6S)-5-(2-methoxy-5-methylsulfonylbenzylamino) -6-diphenylmethyl-1-azabicyclo[2.2.2]octane-3carboxylic acid;

(3R,4S,5S,6S)-5-(5-dimethylamino-2-methoxybenzylamino) -6-diphenylmethyl-1-azabicyclo[2.2.2]octane-3-carboxylic acid;

(3R,4S,5S,6S)-5-(5-isopropyl-2-methoxybenzylamino)-6-diphenylmethyl-1-azabicyclo[2.2.2]octane-2-carboxylic acid;

(3R,4S,5S,6S)-5-(2-methoxy-5-methylthiobenzylamino)-6-diphenylmethyl-1-azabicyclo[2.2.2]octane-2-carboxylic acid;

(3R,4S,5S,6S)-5-(2,5-dimethoxybenzylamino)-6-diphenylmethyl-1-azabicyclo[2.2.2]octane-2-carboxylic acid;

(3R,4S,5S,6S)-5-(2-methoxy-5-methylbenzylamino)-6-diphenylmethyl-1-azabicyclo[2.2.2]octane-2 -carboxylic acid;

(3R,4S,5S,6S)-5-(5-ethyl-2-methoxybenzylamino)-6-diphenylmethyl-1-azabicyclo[2.2.2]octane-2-carboxylic acid;

(3R,4S,5S,6S)-5-(2-methoxyl-5-n-propylbenzylamino)-6-diphenylmethyl-1-azabicyclo[2.2.2]octane-2-carboxylic acid;

(3R,4S,5S,6S)-5-(5-sec-butyl-2-methoxybenzylamino)-6-diphenylmethyl-1-azabicyclo[2.2.2]octane-2-carboxylic acid;

(3R,4S,5S,6S)-5-(5-N-methyl-methanesulfonylamino-2-methoxybenzyl-amino)-6-diphenylmethyl-1azabicyclo [2.2.2]octane-2-carboxylic acid;

(3R,4S,5S,6S)-5-(2-methoxy-5-methylsulfinylbenzylamino) -6-diphenylmethyl-1-azabicyclo[2.2.2]octane-2carboxylic acid;

(3R,4S,5S,6S)-5-(2-methoxy-5-trifluoromethoxybenzylamino) -6-diphenylmethyl-1-azabicyclo[2.2.2]octane-2carboxylic acid;

(3R,4S,5S,6S)-5-(2-methoxy-5-methylsulfonylbenzylamino) -6-diphenylmethyl-1-azabicyclo[2.2.2]octane-2carboxylic acid; and (3R,4S,5S,6S)-5-(5-dimethylamino-2-methoxybenzylamino) -6-diphenylmethyl-1-azabicyclo[2.2.2]octane-2-carboxylic acid;

and the pharmaceutically acceptable salts of the foregoing compounds.

* * * * *

Adverse Decision in Interference

Patent No. 5,576,317, Susan F. Gonsalves, NK-1 RECEPTOR ANTAGONISTS AND 5HT3 RECEPTOR ANTAGONISTS FOR THE TREATMENT OF EMESIS, Interference No. 105,375, final judgment adverse to the patentees rendered, January 18, 2006, as to claims 1-14 Ct. 2.

*(Official Gazette April 25, 2006)*